US009745621B2

United States Patent
Opdahl

(10) Patent No.: US 9,745,621 B2
(45) Date of Patent: Aug. 29, 2017

(54) TEMPERATURE GRADIENT SURFACE PLASMON RESONANCE INSTRUMENT

(71) Applicant: WISYS Technology Foundation, Inc., Madison, WI (US)

(72) Inventor: Aric Martin Opdahl, La Crosse, WI (US)

(73) Assignee: WISYS Technology Foundation, Inc., Madison, WI (US)

( * ) Notice: Subject to any disclaimer, the term of this patent is extended or adjusted under 35 U.S.C. 154(b) by 0 days.

(21) Appl. No.: 15/239,155

(22) Filed: Aug. 17, 2016

(65) Prior Publication Data

US 2017/0052133 A1   Feb. 23, 2017

Related U.S. Application Data

(60) Provisional application No. 62/206,083, filed on Aug. 17, 2015, provisional application No. 62/257,876, filed on Nov. 20, 2015.

(51) Int. Cl.

| | |
|---|---|
| G01N 21/55 | (2014.01) |
| C12Q 1/68 | (2006.01) |
| G01N 21/64 | (2006.01) |
| G01N 21/552 | (2014.01) |
| G01N 21/03 | (2006.01) |
| G01N 21/27 | (2006.01) |
| G01N 21/17 | (2006.01) |

(52) U.S. Cl.
CPC ......... *C12Q 1/6837* (2013.01); *C12Q 1/6825* (2013.01); *G01N 21/0332* (2013.01); *G01N 21/553* (2013.01); *G01N 21/648* (2013.01); *G01N 21/6428* (2013.01); *G01N 21/274* (2013.01); *G01N 2021/1731* (2013.01); *G01N 2201/1211* (2013.01)

(58) Field of Classification Search
CPC ................ C12Q 1/6825; C12Q 1/6837; G01N 21/6428; G01N 21/648; G01N 2021/1731; G01N 2021/6439; G01N 21/0332; G01N 21/274; G01N 21/553; G01N 21/554; G01N 2201/0231; G01N 2201/1211; G01N 2201/127
USPC ................................. 356/432–448
See application file for complete search history.

(56) References Cited

PUBLICATIONS

Hanbin Mao et al.; A Microfluidtc Device with a Linear Temperature Gradient for Parallel and Combinatorial Measurements; Journal of the American Chemical Society 124, No. 16 (2002): pp. 4432-4435. US.

Neil Crews et al.; Spatial DNA Melting Analysis for Genotyping and Variant Scanning, Crews; Analytical chemistry 81, No. 6 (2009): pp. 2053-2058, US.

Yann Marcy et al.; Innovative integrated system for real-time measurement of hybridization and melting on standard format microarrays; Bioteohniques 44, No. 7 (2008): pp. 913-920. FR.

(Continued)

*Primary Examiner* — Tri T Ton
(74) *Attorney, Agent, or Firm* — Boyle Fredrickson, S.C.

(57) ABSTRACT

A system and method for sensitive measurements of molecular binding as a function of time and temperature provided by a surface plasmon resonance (SPR) instrument producing a stable temperature gradient over the sensor surface. Continuous monitoring of reflected light intensity from different locations of the sensor allows simultaneous measurement of time and temperature dependence of binding interactions.

18 Claims, 5 Drawing Sheets

(56) References Cited

PUBLICATIONS

Dongbiao GE et al.; Thermostable DNA Immobilization and Temperature Effects on Surface Hybridization; Langmuir 28, No. 22 (2012): pp. 8446-8455. US.

J. B. Fiche et al.; Point Mutation Detection by Surface Plasmon Resonance Imaging Coupled with a Temperature Scan Method in a Model System; Analytical chemistry 80, No. 4 (2008): pp. 1049-1057. US.

J. Fuchs et al.; Salt Concentration Effects on Equilibrium Melting Curves from DNA Microarrays; Biophysical journal 99, No. 6 (2010); pp. 1886-1895. US.

TEMPERATURE GRADIENT SURFACE PLASMON RESONANCE INSTRUMENT

CROSS REFERENCE TO RELATED APPLICATION

This application claims the benefit of U.S. provisional application 62/257,876 filed Nov. 20, 2015 and U.S. provisional application 62/206,083 filed Aug. 17, 2015 both of which are hereby incorporated by reference.

STATEMENT REGARDING FEDERALLY SPONSORED RESEARCH OR DEVELOPMENT

This invention was made with United States government support awarded by the following agency: National Science Foundation (NSF) 1152042, The United States government has certain rights in this invention.

BACKGROUND OF THE INVENTION

The present invention relates to instruments and methods for the temperature dependent analysis of nucleic acids, peptides, carbohydrates, and the like (hereinafter biological oligomers) and in particular to an instrument that can assist in quantitative analysis of binding interactions of such oligomers.

Measuring the thermodynamics of interactions involving nucleic acids and peptides is a vital component of biomolecular studies. Conventionally, these properties are analyzed in solution by temperature dependent spectroscopic measurement (e.g., UV-vis, CD, fluorescence) or thermal methods (ITC, DSC). See generally (1) Mergny, J. L.; Lacroix, L. Oligonucleotides 2003, 13, 515-537 and Jelesarov, I.; Bosshard. H. R. J. Mol. Recognit. 1999, 12, 3-18. For example, DNA thermal denaturation profiles obtained by monitoring changes in UV absorption as the temperature of the solution is incremented can be used to generate robust models for predicting the stabilities of DNA structures in solutions.

Surface-based diagnostics, such as surface plasmon resonance (SPR), have been used to provide analysis of binding kinetics and affinities of biomolecular interactions at a single temperature. In SPR, a nanoscale thin metallic film is illuminated from the back "reflecting side" of the film. At a certain angle, known as the plasmon angle, the energy from the illumination is coupled into electromagnetic waves creating a resonant condition (surface plasmon resonance) that is highly sensitive to surface conditions on the "sensing side" of the film opposite to the reflecting side. To the extent that SPR can directly detect linking between probe molecules on the film and target molecules in a solution, largely eliminates the need to use fluorescent or enzymatic tags for monitoring such linking.

Specifically, in SPR imaging, multiple probe spots of a micro-array may be analyzed in parallel, with different biological oligomer probes attached over the surface. In this technique of SPR imaging, p-polarized light impinges on a prism, a gold thin film, and a flow cell assembly at a fixed angle. The reflected light is passed through a narrow band pass filter and collected by a CCD camera. In this technique, probe molecules are covalently linked to discrete positions on the sensing side of the film to selectively bind with target molecules in the solution to be analyzed. The binding of the targets to the surface bound probes causes localized changes in the index of refraction at those spots, which are detected by the CCD camera. This data can then be used to identify the presence and composition of the target molecules by the location of the detected binding event.

SPR experiments can be repeated at different temperatures to provide a better understanding of interactions between biological oligomers, for example, indicating the temperatures at which binding interactions occur or providing plots showing how sensor binding kinetics varies with temperature. Because SPR measurements are highly sensitive to temperature variation, for each experiment the SPR apparatus is normally stabilized to a uniform temperature. Changing this uniform temperature between measurements is normally accompanied by an extended stabilization time during which the apparatus acclimates to a uniform and precise temperature greatly slowing the acquisition of data.

SUMMARY OF THE INVENTION

The present invention provides an SPR instrument that can create a stable and precise thermal gradient across its sensing surface allowing parallel measurements at different temperatures to be simultaneously received, greatly speeding the measurement process. Although the temperature across the sensing surface varies, the temperature at any specific location can be held constant allowing established SPR techniques to quantify biological oligomer interactions by separating out changes in reflectivity caused by molecular associations and disassociations from changes in reflectivity caused by changes in temperature. The temperature profile of the gradient is determined through a calibration process developed for the specific apparatus.

Specifically then, one embodiment of the invention provides an apparatus for evaluating interactions between biological oligomers having a light source, a camera, and an optical coupler positioned between the light source and the camera to receive light from the light source for reflection from an active face of the optical coupler to be received by the camera. A metal film extends along a measurement plane proximate to the active face for holding oligomers subject to interaction on a first face of the metal film, and a flow channel opens against the first face of the metal film for receiving a liquid flow in a direction therealong. First and second thermal stabilizers are positioned in thermal communication with the metal film and separated along the measurement plane near opposite edges of the metal film and adapted to establish a predetermined and substantially constant temperature gradient along the metal film.

It is thus a feature of at least one embodiment of the invention to provide a mechanism for rapid acquisition of temperature-related phenomenon using a temperature gradient that is sufficiently stable to prevent the introduction of confounding temperature errors. By providing a sufficiently constant flow rate through the flow channel and low thermal impedance thermal stabilizers, the present inventor has determined that a sufficiently stable temperature gradient can be produced for this purpose.

The apparatus may include a controller attached to the first and second thermal stabilizers for controlling the first and second thermal stabilizers in a first state to have different temperatures to establish a substantially constant temperature gradient along the metal film and in a second state to have identical temperatures to establish a gradient-free, substantially constant temperature along the metal film.

It is thus a feature of at least one embodiment of the invention to provide a versatile temperature control that allows both the measurement of temperature-sensitive binding experiments and that permits development of the necessary calibration curves enabling this precise measurement.

The thermal stabilizers may be separated along the direction of fluid flow to establish a temperature gradient in the direction of fluid flow. The thermal stabilizers may also be separated in a direction orthogonal to the direction of fluid flow to establish a temperature gradient across the sensor.

It is thus a feature of at least one embodiment of the invention to provide longitudinally consistent temperature gradients perpendicular to the fluid flow for simplifying data averaging and the like.

The apparatus may include an electronic computer operating to: (a) image reflectivity from the active face of the optical coupler at multiple points over at least one dimension on the surface of the second face aligned with the temperature gradient; and (b) compare the imaged reflectivity to gradient calibration data indicating a temperature associated with each of the multiple points to provide an indication of binding as a function of temperature.

It is thus a feature of at least one embodiment of the invention to accommodate arbitrary but temporally constant gradient shapes through the use of calibration curves indicating the temperature at different points on the surface of the active face of the optocoupler.

The camera may image reflectivity of the active face of the optical coupler in two dimensions, a first dimension parallel to a temperature gradient, and a second dimension perpendicular to the temperature gradient, and the computer may combine data along the second dimension before analysis.

It is thus a feature of at least one embodiment of the invention to provide more robust measurements through the ability to combine data sampled across the fluid flow such as experience a similar temperature.

The flow cell may include at least one flow path along the metal film and where the flow cell is split into additional channels separated by a wall preventing mixing of liquid between each flow path. Each additional channel may include a binding material to interact with a biological oligonucleotide on the test surface. The electronic computer may further image reflectivity from the active face of the optical coupler at multiple points over at least one dimension on the active face aligned with the temperature gradient images for each of the flow paths and may use multiple points to deduce temperature along each flow path for establishing the gradient calibration data.

It is thus a feature of at least one embodiment of the invention to allow different analyte solutions to be flown over the sensor at the same time, facilitating parallel measurement of solutions (efficiency).

A first channel may have a binding material and a second channel may not contain binding material, thus, the second channel is used as reference for background subtraction.

It is thus a feature of at least one embodiment of the invention to permit measurements for generating temperature gradient calibration data. One of the flow cell channels can be used as a reference channel to act as "background" or reference. The background subtraction accounts for things like change in brightness of the light source or sensitivity of the camera over time.

The stored program may provide a display outputting information providing indication of binding as a function of both time and temperature.

It is thus a feature of at least one embodiment of the invention to permit simultaneous measurements over a range of temperatures as a function of time.

The first and second thermal stabilizers may be associated with temperature sensors and control circuitry to operate the first and second thermal stabilizers in closed loop fashion to provide predetermined temperatures.

It is thus a feature of at least one embodiment of the invention to provide extremely precise temperature control possible with high gain feedback.

The flow channel may have a thermal conductivity of at least 0.8 W/mK.

It is thus a feature of at least one embodiment of the invention to increase the thermal connection between the thermal stabilizers and the flowing liquid by pre-tempering the liquid flowing past the test surface for greater flexibility in temperature range measurement.

These particular objects and advantages may apply to only some embodiments falling within the claims and thus do not define the scope of the invention.

DETAILED DESCRIPTION OF THE PREFERRED EMBODIMENT

Figure 1:
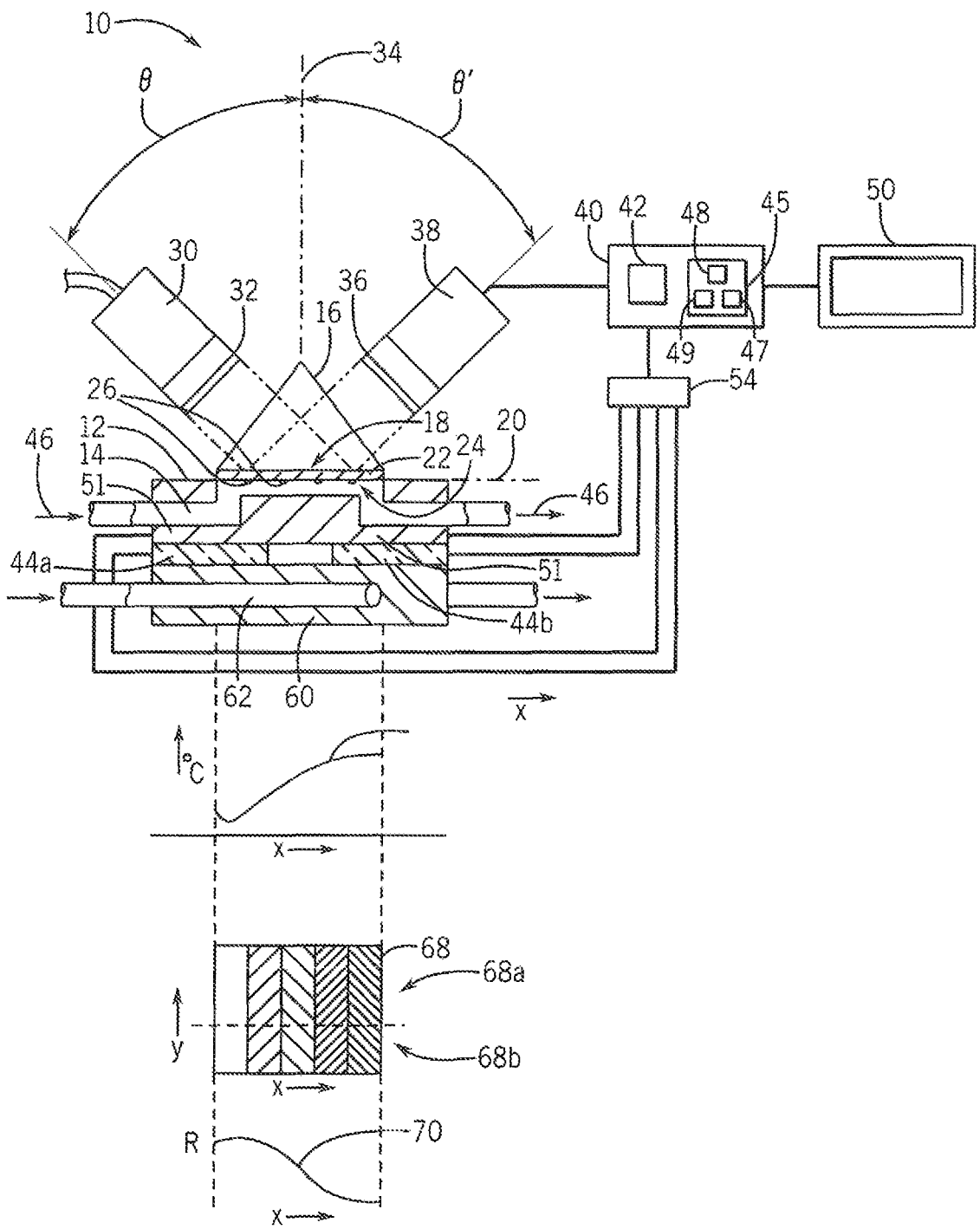
FIG. 1 is a cross-sectional view of an apparatus constructed according to the present invention showing an optical coupler communicating between a light source and camera to measure reflected light in the optical coupler adjacent to metal film where metal film is exposed to a flow channel, and showing thermal stabilizers positioned along the flow channel for establishing a thermal gradient at the metal film, and further showing the temperature profile of the thermal gradient, a simplified image collected by the camera, and measured reflectance from that image, as well as a connected computer and display for displaying output data.

Referring now to FIG. 1, a temperature gradient surface plasmon resonance (SPR) device 10 may include a flow conduit 12 providing a channel 14 conducting a fluid along an x-axis direction. An upper wall of the channel 14 opens toward a transparent optical coupler 16, for example, a right angle prism, whose base 18 defines a measurement plane 20.

Attached to or proximate to the base 18 is a metal film 22 (shown greatly exaggerated for clarity), for example, of metallic gold. The metal film 22 is sized to support plasma waves on its lower active surface 24 as stimulated by evanescent waves from light internally reflected off of the base 18 of the optical coupler 16.

The upper wall of the channel 14 is sized so that a lower active surface 24 of the metal film 22 facing the channel 14 is in contact with a fluid within the channel 14. This lower active surface 24 may be spotted at probe locations with probe molecules 26 such as biological oligomers in a regular pattern over two dimensions within the measurement plane 20. For a 15 nucleotide probe sequence as the probe molecule 26, an average spacing of about three nanometers between probes provides the optimal combination of sensor activity and hybrid stability. This spacing can be identified by using the present invention to monitor binding strength as a function of spacing. A spacing may then be enforced for example through co-adsorption with a second component that acts as a lateral spacer.

A collimated light source 30 (for example, white light) is positioned to direct light through a first upward sloping face of the optical coupler 16 to illuminate an active area of the base 18 stimulating plasmon activity in the metal film 22 adjacent to the base 18 over which the probe molecules 26 are dispersed. Before being received by the optical coupler 16, the light passes through a monochromator/polarizer 32 which filters the light to a desired narrowband frequency and provides polarization as is generally understood in the art. The light from the light source 30 strikes the base 18 at an adjustable angle θ with respect to a normal 34 to the measurement plane 20. Either or both of the angle θ and the frequency of light from the collimated light source 30 may be adjusted, the latter, for example, by using various bandpass filters (e.g. 770 nanometers, 780 nanometers, 790 nanometers) or other frequency adjustments. These changes may be used to optimize the percent reflectivity value over the temperature gradient as discussed below.

A portion of the light striking the base 18 is coupled into plasmons in the metal film 22. The remaining light reflects internally off the base 18 at an angle θ' equal and opposite to angle θ, to be received through a narrow band pass filter 36 by a CCD camera 38. The CCD camera 38 is focused on the measurement plane 20 of the base 18 to provide an image of the reflected light from the base 18.

In one embodiment, the light source 30 may be a tungsten halogen light source and the monochromator/polarizer 32 may provide for a 1200 groove/mm grating with a 750 nm blaze to provide a narrow band light within the range from 770 to 800 nanometers. The light source 30 may include optics to collimate the light source to an approximately 1 in. diameter beam. The CCD camera 38 may provide for a CMOS image sensor running a resolution of approximately 600 by 490 lines with a 35 mm lens. The filter 36 may provide a 785 nm bandpass filter (FWHM=45 nm) to reduce stray light, while still allowing use of monochromated light ranging from 770 to 800 nm.

The flow conduit 12 may be constructed of stainless steel having a total channel volume of less than 20 μL to provide uniform flow of liquid at flow rates of less than 50 UL/min using a peristaltic pump (not shown). The peristaltic pump may be associated with flow-smoothing elements such as accumulators and flow restrictors of a type known in the art to provide a nearly constant flow through the flow conduit 12.

The CCD camera 38 may communicate with an electronic computer 40 including a processor 42 reading and writing data with a memory 45 holding a stored program 48 whose operation will be described below. Memory 45 may also include calibration curves 47 and measurement data 49 to be acquired by the SPR device 10 as will be discussed below. This measurement data 49 may be displayed on an attached display 50 providing for graphic display capabilities.

Positioned against the lower surface of the flow conduit 12, in thermal communication therewith and thus in thermal communication with the liquid 46 in the flow conduit 12 and the metal film 22, are first and second thermal stabilizers 44a and 44b. In one embodiment the first and second thermal stabilizers 44a and 44b may be Peltier devices receiving DC electrical power controlled in polarity and/or voltage by a temperature controller 54 providing feedback regulation of the voltage and current to the Peltier devices (and hence constant temperature) under the higher level control of the electronic computer 40. The thermal stabilizers 44a and 44 are displaced along the measurement plane 20 to be positioned beneath opposite sides of the metal film 22 so to apply a thermal gradient to the metal film 22 along the measurement plane 20 in the direction of fluid flow through the flow conduit 12.

Generally thermal stabilizer 44a will be biased to cool the lower surface of the flow conduit 12 on an entrance side of the flow conduit 12 that receives liquid 46, whereas thermal stabilizer 44b will be biased to provide heat to a lower surface of the flow conduit 12 on a exit side of the flow conduit 12 out of which liquid flows. Temperature sensing elements 51 may be positioned at an interface between the thermal stabilizers 44 and the flow conduit 12 to measure temperature of the flow conduit 12 and to allow closed-loop temperature control of the flow conduit 12. For this purpose, the temperature sensing elements 51 provide feedback signals to the temperature controller 54 which may then control the thermal stabilizers 44, for example, by controlling the voltage or duty cycle of the voltage, independently for each thermal stabilizer 44 to provide a desired temperature value.

The construction of a flow conduit 12 from highly conductive metal such as stainless steel having a thermal resistance of at least 12 W/mK, or an even a more conductive material, and the positioning of portions of the channel 14 before and after its contact with the metal film 22 near the thermal stabilizers 44, helps provide for a pre-cooling and post-heating of the liquid 46 flowing through the channel 14 by the thermal stabilizers 44. Glass having a thermal resistance of 0.8 W/mK may also be used. This pre-cooling and post-heating reduces the effect of liquid flow on the temperature gradient established between the thermal stabilizers 44 and provides greater versatility in the starting and ending temperatures of the temperature gradient.

In one embodiment, thermal stabilizers 44 may each be 24-watt rectangular thermoelectric/Peltier modules mounted underneath the flow cell and separated from each other by approximately 6 mm, with the temperature of each monitored using 10 kΩ thermistors embedded in the body of the flow conduit 12 directly above each thermal stabilizer 44.

A water cooling block 60 having an internal channel 62 for receiving a flow of temperature regulated water is mounted in thermal contact with the lower surface of the thermal stabilizers 44 opposite its contact with the flow conduit. This water cooling block 60 provides a source or sink for excess heat. Heating of the opposite ends of the flow conduit 12 over the range 20 to 80° C. (±0.02° C.) may be achieved.

In this way, the SPR device 10 may be operated during flow of liquid 46 to provide a temperature gradient 64 as a function of distance along the x-axis along the lower surface of the metal film 22 varying between approximately 20 degrees centigrade at the leftmost edge (as depicted) of the metal film 22 exposed to the channel 14 to about 60 degrees centigrade at the rightmost edge (as depicted) of the metal film 22 exposed the channel 14. The temperature gradient may be approximately linear, but linearity is not required.

The light source 30 (and optics) and camera 38 (and optics) are attached to independent motorized rotation stages (not shown) to allow adjustment of the angles θ of the light and its frequency under control of electronic computer 40.

Figure 2:
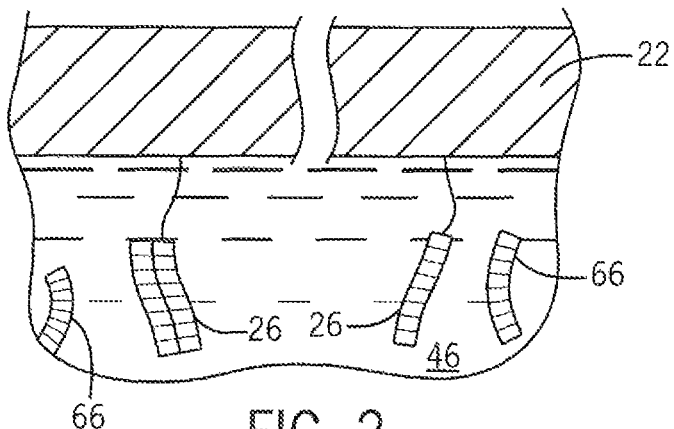
FIG. 2 is a simplified depiction of different oligomer binding behavior as a function of temperature along the metal film.

Referring now to FIG. 2, during operation, the liquid 46 flowing past the lower active surface 24 of the metal film 22 may suspend biological oligomers 66 that may bind with the probe molecules 26 attached to the lower surface of the metal film 22. The amount of binding will depend on the local temperature of the liquid and probe molecules 26 and 66 along the temperature gradient along the metal film 22.

The different amounts of binding will be detectable in changes in the index of refraction in the environment adjacent to the lower surface of the metal film 22 in the vicinity of the probe molecules 26. These changes in index of refraction will change the amount of reflected light at the base 18 of the optical coupler 16 through the mechanism of surface plasmon resonance. In turn, this change in reflected light will be captured in a reflection image 68 by the camera 38 measuring at different pixels of the reflection image 68 different intensities of reflected light. Generally these intensities will vary along the x-axis because of the effect of the temperature gradient on the binding interaction.

The quantitative assessment of this image 68 along any line parallel to the x-axis will yield a reflection curve 70 showing generally (for example) greater reflection with greater binding. Analysis of this reflection curve 70, for example, may be used to determine the temperatures at which binding occurs by looking for a location along the x-axis showing an abrupt change in light reflection related to binding and relating that x-axis location to a temperature per the temperature gradient. This temperature provides insight into the binding strength of the probe molecules 26 and 66.

The time evolution of the image 68 permits a second measurement of binding kinetics, for example, showing how the binding changes with time as fluid flows through channel 14.

Data related both to binding kinetics and binding strength may be simultaneously displayed on the display 50 (shown in FIG. 1) in the form of a three-dimensional representation 72 providing a measure of binding (for example, per reflection) along a vertical axis and time in temperature along two orthogonal horizontal axes.

Figure 3:
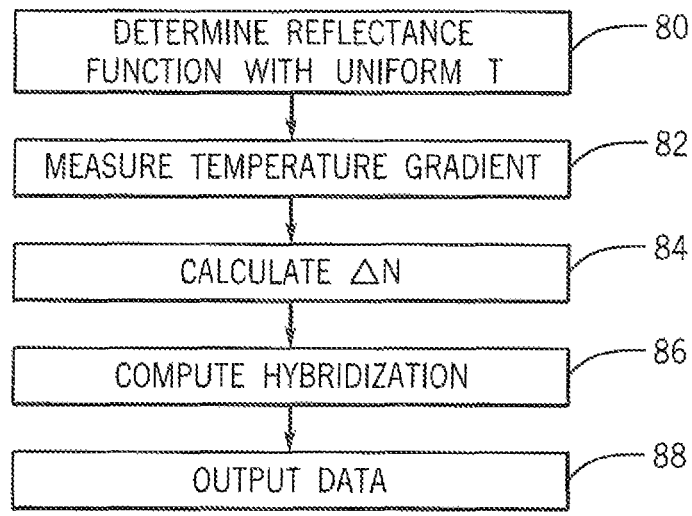
FIG. 3 is a flowchart of the steps for calibrating and using the apparatus of FIG. 1.

Referring now to FIGS. 1 and 3, because the light reflected off of the base 18 will be dependent both on binding to the sensor and on the temperature of the liquid 46 at each point along the base 18, it is necessary to know the temperature gradient 64 with high accuracy so as to be able to separate these two effects. For this reason, use of the SPR device 10 will be preceded by a calibration procedure producing one or more calibration curves 47 that can be held in the memory 45 and used to provide necessary calibration to the SPR device 10. Generally these calibration curves 47 will provide for data necessary to accurately determine the temperature gradient 64 and will also include other measurements used to convert reflectivity into a measure of binding as will be discussed.

As indicated by process block 80, a first set of calibration curves 47 establishes the relationship between the temperature of the liquid 46 and reflectivity necessary to measure temperature gradient 64 across the lower active surface 24 using reflectivity. In this calibration process both thermal stabilizers 44a and 44b are controlled to provide the same temperature eliminating the gradient across the metal film 22. A solution approximating that which will be used during binding experiments (that is, without the biological oligomers) is then passed through the channel 14 and reflectance measured using the camera 38. After each reflectance measurement, the temperature of the thermal stabilizers 44a and 44b are incremented so that a set of reflectance values may be obtained for a range of temperatures, for example, from 20 to 60 degrees Celsius.

The liquid 46, for this purpose may be an aqueous solution of specific ionic strength and acidity. An example is NaCl-TE containing between 0.1 and 1.0 moles per liter of sodium chloride and trace amounts of Tris-HCL and EDTA adjusted to a pH of 7.

As indicated by process block 82 these temperature/reflectance values are then used to measure the actual temperature gradient 64 to be provided by the thermal stabilizers 44a and 44b by adjusting each of the thermal stabilizers 44 to different temperatures (for example, to 20 degrees for thermal stabilizer 44a and to 60 degrees for thermal stabilizer 44b, respectively) and flowing the same liquid NaCl-TE along the metal film 22 to collect reflectivity measurements. At this time, the reflectivity will generally vary in the image 68 as a function of position along the x-axis. These reflectivity measurements may then be matched to corresponding reflectivities for particular temperatures per the previously acquired calibration data 47 to deduce the temperature gradient 64. This temperature gradient 64 may provide a temperature gradient calibration data 47 also stored in the memory 45.

At process block 84, measurement of sensor binding may employ successive measurements made with three different liquids 46a, 46b and 46c. The first two liquids 46a and 46b each provide an oligomer-free solution, for example, of sodium chloride as described above. A first of these two liquids 46a will be substantially identical to the third liquid 46c used during the binding process being investigated while a second of these two liquids 46b will have a slightly different index of refraction, for example, containing an additional 0.050 moles per liter of sodium chloride. The refractive indices of these liquids 46a (and 46c) and 46b may be determined by separate measurements (for example, using an Abbe refractometer) to determine the refractive indices $n_1$ and $n_2$.

A third measurement is then made using liquid 46c being substantially identical to the first of the two liquids 46a but also including the reacting oligomer 66 shown in FIG. 2. Each of these measurements produces an image 68 that may be stored in memory 45.

A change of index $\Delta n_{hyb}$ each point of the images 68 may then be computed by combining the intensities of reflectivities measured by each of these images 68 as follows:

$$\Delta n_{hyb} = \left(\frac{I_{hyb} - I_1}{I_2 - I_1}\right) \times (n_2 - n_1) \qquad (1)$$

where $I_1$, $I_2$ and $I_{hyb}$ are the measured intensities of reflection (at corresponding points in each image 68) for each of the oligomer-free liquids 46a, 46b, and 46c, respectively, and $n_1$ and $n_2$ are the indices of refraction of the oligomer-free liquids 46a (and 46c) and 46b, respectively.

At process block 86 an amount of sensor binding, may be computed using the following formula (for example, for a DNA hybridization measurement where probe molecules 26 and 66 are DNA oligomers and sensor binding is reported as hybrids-$cm^2$):

$$\text{hybrids} \cdot \text{cm}^{-2} = \left(\frac{l_d}{2}\right) \times \left(\frac{\Delta n_{DNA}}{n_{DNA} - n_b}\right) \times \left(\frac{\rho_{DNA} \times N_A}{MW}\right)$$

where:

$l_d$ is the decay length of the evanescent wave after reflection of light in the optical coupler 16 (estimated to be 350 nanometers if the light wavelength is 780 nanometers);

$n_a - n_s$ is the difference in index of refraction between the liquid 46c ($n_a$) containing the oligomer 66 and liquid ($n_s$) not containing the oligomer 66 (estimated to be 1.7);

$\rho_{DNA}$ is the bulk density of the oligomer (estimated to be 1.7 grams/cm$^3$ for DNA);

MW is the molecular weight of the oligomer.

Figure 4:
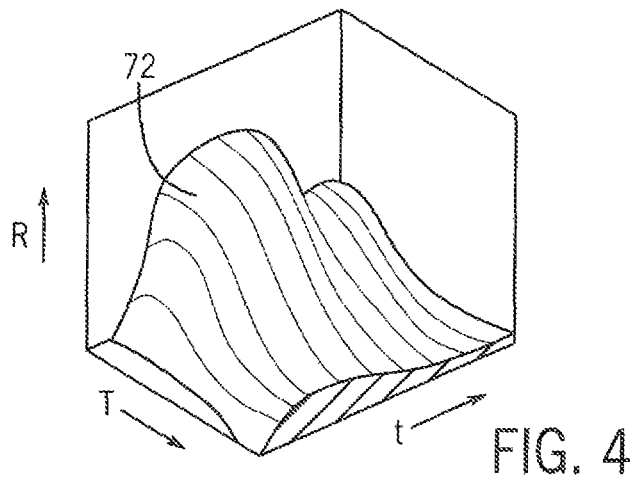
FIG. 4 is an example graph output on the display of FIG. 1 providing both binding kinetics and strength measurements.

At process block 88, these values hybrids·cm$^{-2}$ characterized for each point of the image 68 (or another reflectance-based value) may be output, for example, in the form of the graph shown in FIG. 4. Quantitative representations of these values hybrids·cm$^{-2}$ in the form of tables or the like or two-dimensional graphs representing cross-sections through the three-dimensional figure shown in FIG. 4 may also be provided.

During each of these measurements of reflectance, the angles θ and θ' may be adjusted to provide maximum sensitivity to temperature changes in the central portion of the gradient. Desirably the angles θ are set to provide a percentage of reflectivity of between 30 and 60 percent of its maximum value. It will be appreciated that optical systems can be developed to allow separate angles to be provided for different x-axis portions of the gradient. Alternatively, measurements may be made at multiple angles or wavelengths of light for different portions of the gradient.

Each of these measurements also may be repeated using different wavelengths of light, for example, 780 nanometers, 770 nanometers, and 790 nanometers affecting each of the process blocks 80, 82, and 84 for providing higher accuracy at the beginning and ending of the gradient. Data from multiple measurements may be combined using statistical techniques such as averaging. Further, data sampled along points of constant x-axis (for example, along the y-axis) may be combined, for example, by averaging to improve these measurements. When computing the temperature gradient 64, the temperature data may be fit to a sigmoidal equation to provide a temperature for each point along the y-axis.

Figure 5:
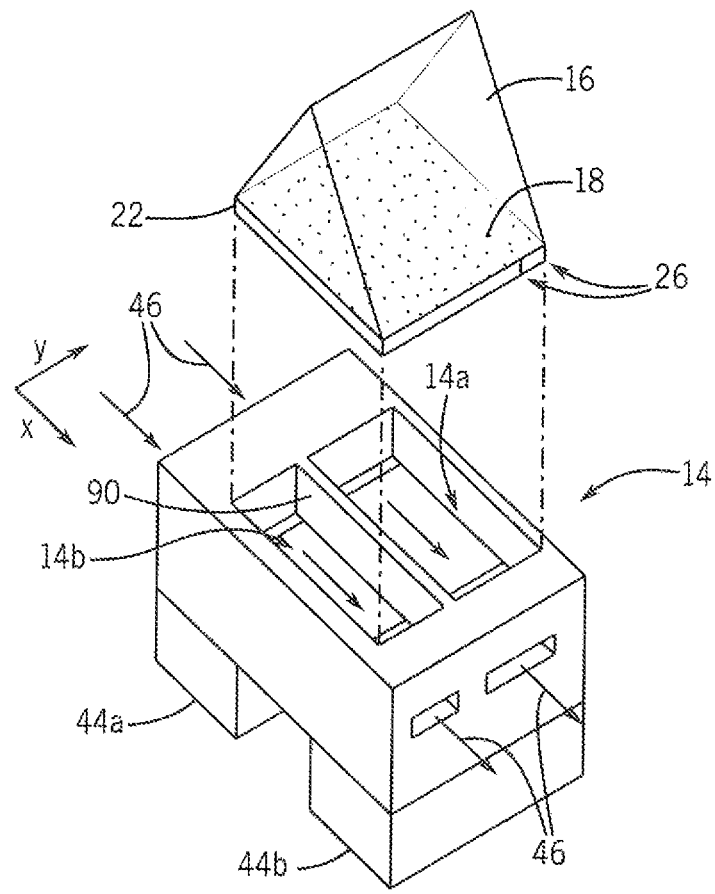
FIG. 5 a perspective view of the apparatus of FIG. 1 showing the use of separate flow channels for dynamic calibration.

Referring now to FIG. 5, in one embodiment, the channel 14 may be split into two parallel channels 14a and 14b divided by a wall 90 extending longitudinally along the direction of fluid flow and separating the channels 14a and 14b to prevent intermixing of the fluid flow in the parallel channels 14a and 14b. Reflectance data above each of parallel channels 14a and 14b may be separately imaged as image portions 68a and 68b shown in FIG. 1.

During process block 84, when the sensor binding experiment is being performed, the oligomer 66 may be introduced only in the channel 14a, and channel 14b used for the purpose of monitoring real time changes attributed to small temperature variations or other instrumental parameters.

Figure 6:
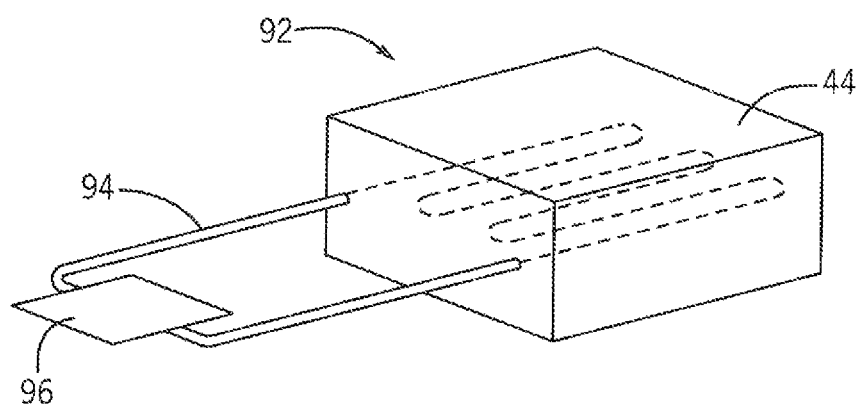
FIG. 6 is a perspective representation of an alternative thermal stabilizer using heat exchanger blocks.

Referring now to FIG. 6, it will be appreciated that the thermal stabilizers 44 need not be Peltier devices but may make use of any known thermal stabilization technique, for example, using heat exchangers 92 receiving circulated liquid through conduits 94 communicating with a reservoir 96 of temperature stabilize liquid, the latter temperature controlled, for example, by conventional heater thermostat systems or chillers known in the art.

Figure 7:
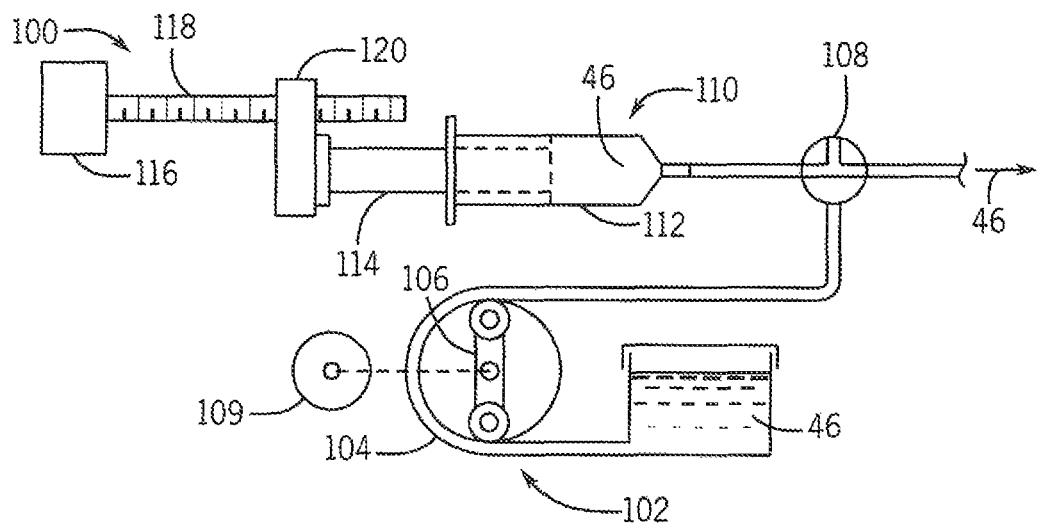
FIG. 7 is a diagram of a pump system for providing constant flow rates to the flow channel of FIG. 1.

Referring now to FIGS. 1 and 7, the stability of the temperature gradient 64 is strongly influenced by the constancy of the flow rate of solution along the metal film 22. In one embodiment, the invention contemplates a hybrid pump system 100 providing liquid 46 for introduction into the channel 14. The hybrid pump system 100 includes a peristaltic pump 102 feeding liquid 46 from a reservoir through a flexible tube 104 progressively compressed by a roller mechanism 106 to pinch off the tube 104 and propel the contained liquid toward a diverter valve 108 which may be set to send the liquid to the channel 14. The roller mechanism 106 may be powered by a constant speed DC electric motor 109. This mode may be useful for calibration processes where constant temperature liquid is required and hence slight pulsation or variation in the flow rate may be tolerated. During temperature gradient measurements, diverter valve 108 is changed in position to provide a source of liquid to the channel 14 from a syringe pump 110 having a syringe 112 containing liquid 46. The plunger 114 of the syringe 112 is advanced by means of a motor 116, for example, driving a lead screw 118 and follower 120 or the like to expel liquid from the syringe 112. The general linear and continuous nature of the syringe pump 110 is believed to provide a more consistent flow rate without the need for accumulating reservoirs or the like such as increase the needed sample size.

Figure 8:
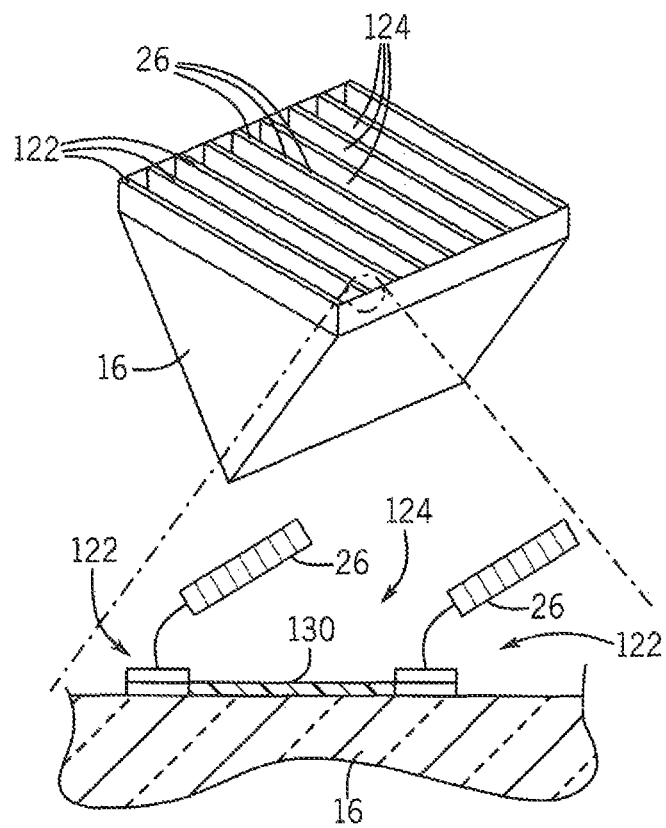
FIG. 8 is a perspective view and fragmentary cross-section of a bottom surface of the optical coupler providing a striping of probe molecules for refined parallel binding measurements.

Referring now to FIG. 8, the flow channels 14a and 14b provided in the embodiment of FIG. 5 can contain multiple linear regions 122 of probe molecules 26 separated by empty exclusion rows 124 that serve to establish multiple zones providing the image portions 68a-68e (only a limited number of portion shown for clarity) for the purpose of temperature correction described above with respect to FIG. 5. That is, imaging of the exclusion rows 124 may be used to monitor changes in background values and imaging of the individual linear regions 122 may be used to simultaneously determine binding of the probe molecules 26 in each region. For this purpose, the electronic computer 40 uses a mask applied to the acquired image and separating these two regions for different analysis purposes. In addition, each of the linear regions 122 may have the same or different probe molecules 26 for parallel analysis of different systems.

The linear regions 122 may be created, for example, by selective application of materials and probe molecules 26 to the bottom of the optical coupler 16. In one embodiment, the process may be an additive process employing a mask. For example, a two nanometer titanium layer 126 and a 50 nanometer gold layer 128 may be applied selectively to linear regions 122 of the lower surface of the optical coupler 16 through the use of a shadow mask. Alternatively, these linear regions 122 may be created by an etching process using a photoresist and projected mask. The probe molecules 26 are then adsorbed onto the surface of the gold layer 128. Alternatively, linear regions 122 may be created, for example, by applying a passivating layer 130 that is resistant to nonspecific adsorption of DNA such as oligo(ethylene) glycol or mercaptohexanol, and exposing the sample to UV light through a mask to degrade the passivating layer. The probe molecules 26 are then adsorbed onto the surface of the exposed gold layer 128. These probes may then be used in the process described above with respect to FIGS. 1-4.

Figure 9:
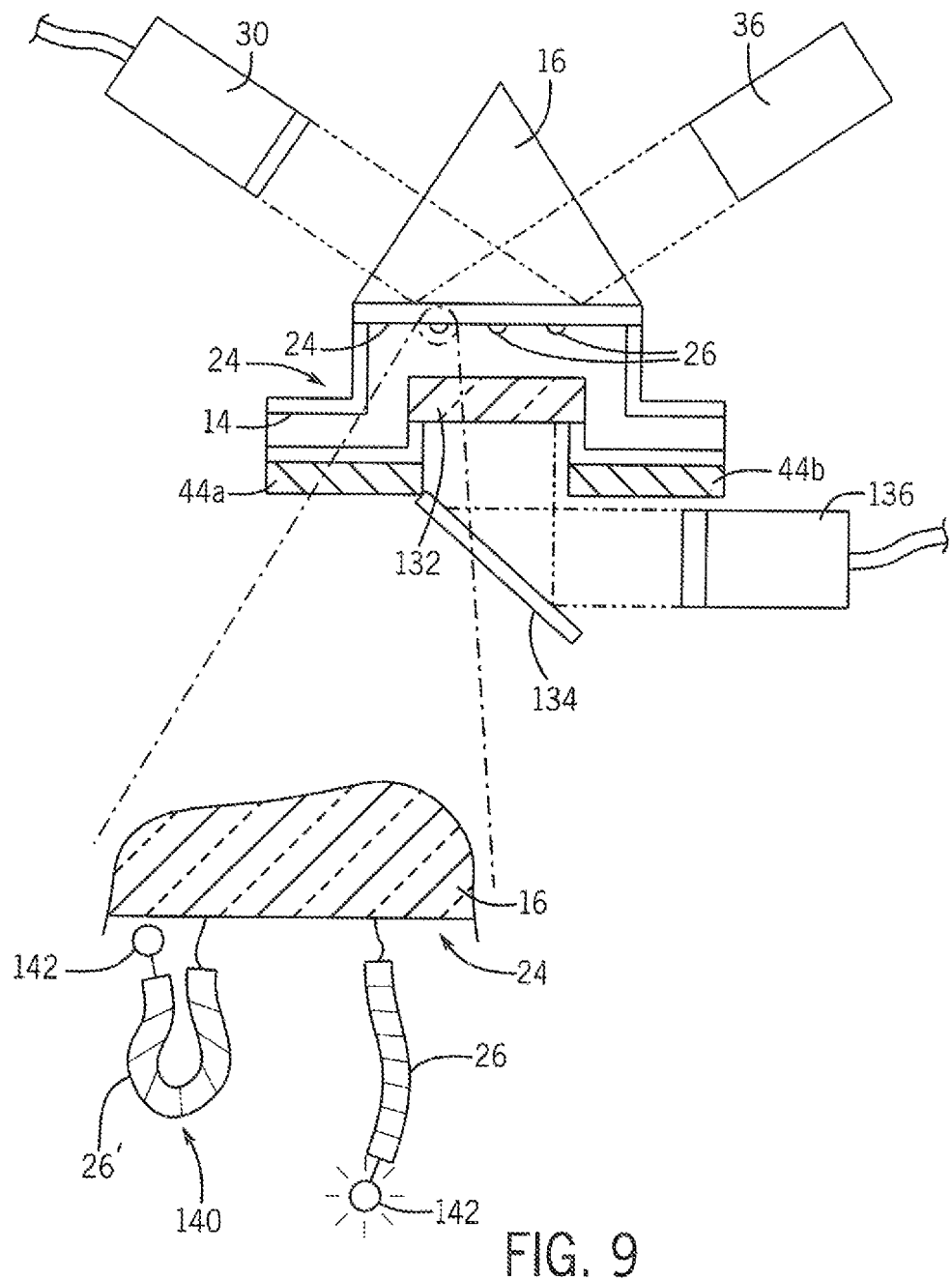
FIG. 9 is a figure similar to that of FIG. 1 showing an alternative flow cell arrangement useful for surface plasmon enhanced fluorescence spectroscopy (SPFS) and otherwise identical to FIG. 1.

Referring now to FIG. 9, the present invention can also be adapted for use with surface plasmon enhanced fluorescence spectroscopy (SPFS) measurements by constructing a lower wall 132 of the conduit 12 beneath the metal film 22 from an optically transparent material. This optically transparent material allows light from fluorescent materials associated with the probe molecules 26 to pass downward through the lower wall 132, for example, to a reflector 134 to be received by a camera 136. SPFS senses fluorescing molecules that are in the region beyond the Förster radius but within the evanescent wave penetration depth (i.e., between approximately 10 nm and 200 nm from the surface 24 of the gold metal film 22). For example, SPFS measurements of probe molecules 26 in the form of hairpin DNA probes 140, can have a distal end functionalized with a fluorescent tag 142 such as WellRED D2 or IRDye800. This fluorescent tag 142 would be expected to yield a small fluorescence signal at low temperatures where the hairpin is closed (shown by probe molecule 26') because of quenching from the gold of metal film 22. The fluorescence signal would increase at high temperature when the hairpin opens because the fluorophore tagged end of the strand extends further from the surface 24. SPFS can also be used to measure sensor responses from fluorescently labelled analytes, and in such instances would be complementary to reflectivity measurements.

Generally, the above described invention is not limited to the analysis of DNA or hybridization but may make measurements of other binding energies and drug interactions. For example, the present invention may be used to characterize the binding between small molecules and hybridized DNA structures. Small molecules that intercalate into the double helix structure of DNA are important for biological processes including gene regulation and have pharmacological applications as antitumor agents. The present invention may also be used to characterize binding of nanoparticles functionalized to bind with probes on the gold surface 24 such as will cause an abrupt change in index of refraction.

Certain terminology is used herein for purposes of reference only, and thus is not intended to be limiting. For example, terms such as "upper", "lower". "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

The term "constant gradient" should be understood to refer to a constant spatial gradient shape with respect to time and is not limited to a gradient with a constant first derivative or linear slope.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microprocessor" and "a processor" or "the microprocessor" and "the processor," can be understood to include one or more microprocessors that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more processor-readable and accessible memory elements and/or components that can be internal to the processor-controlled device, external to the processor-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications are hereby incorporated herein by reference in their entireties.

I claim:

1. An apparatus for evaluating interactions between biological oligomers comprising:
   a light source;
   a camera;
   an optical coupler positioned between the light source and the camera to receive light from the light source for reflection from an active face of the optical coupler to be received by the camera;
   a metal film extending along a measurement plane proximate to the active face for holding oligomers subject to interaction on a first face of the metal film;
   a flow channel opening against the first face of the metal film for receiving a liquid flow in a direction therealong; and
   a first and second thermal stabilizer positioned in thermal communication with the metal film and separated along the measurement plane near opposite edges of the metal film and adapted to establish a predetermined and substantially constant temperature gradient along the metal film.

2. The apparatus of claim 1 further including a controller attached to the first and second thermal stabilizer for controlling the first and second thermal stabilizers in a first state to have different temperatures to establish a substantially constant temperature gradient along the metal film and in a second state to have identical temperatures to establish a gradient-free substantially constant temperature along the metal film.

3. The apparatus of claim 1 wherein the thermal stabilizers are separated to establish a temperature gradient across the sensor.

4. The apparatus of claim 1 further including an electronic computer communicating with the camera and executing a stored program held in non-transitory medium to:
   (a) image reflectivity from the active face of the optical coupler at multiple points over at least one dimension on the active face aligned with the temperature gradient; and
   (b) compare the imaged reflectivity to gradient calibration data indicating a temperature associated with each of the multiple points to provide an indication of binding as a function of temperature.

5. The apparatus of claim 4 wherein the stored program at step (a) images reflectivity of the active face of the optical coupler in two dimensions, a first dimension parallel to a temperature gradient and a second dimension perpendicular to the temperature gradient, and including the step of combining data along the second dimension before step (b).

6. The apparatus of claim 4 wherein the flow cell includes at least one flow path along the metal film and where the flow cell is split into additional channels separated by a wall preventing mixing of liquid between each flow path.

7. The apparatus of claim 6 wherein each additional channel may include a binding material interacting with a biological oligonucleotide on the metal film.

8. The apparatus of claim 6 wherein the electronic computer further executes the stored program to:
   at step (a) image reflectivity from the active face of the optical coupler at multiple points over at least one dimension on the active face aligned with the temperature gradient images for each flow path; and
   at step (b) use the multiple points to deduce temperature along each flow path for establishing the gradient calibration data.

9. The apparatus of claim 4 wherein the electronic computer further executes the stored program to provide a display outputting information providing an indication of binding as a function of both time and temperature.

10. The apparatus of claim 1 wherein the first and second thermal stabilizers are associated with temperature sensors and control circuitry to operate the first and second thermal stabilizers in closed loop fashion to provide predetermined temperatures.

11. The apparatus of claim 10 wherein the thermal pumps are Peltier devices.

12. The apparatus of claim 10 wherein the thermal pumps are heat exchangers communicating with temperature-controlled fluid reservoirs.

13. The apparatus of claim 1 wherein the flow channel has a thermal conductivity of at least 0.8 W/mK.

14. The apparatus of claim 1 further including a hybrid pump communicating with the flow channel to pump fluid to create the liquid flow, where in the hybrid pump includes a first pump limited, during operation to create the liquid flow, to a single pump cycle in which a predetermined volume of liquid may be expelled from a pump chamber and a second pump substantially unlimited, during operation to create the liquid flow, to provide multiple pump cycles in which an indefinite volume of liquid may be expelled repeatedly from a pump chamber.

15. The apparatus of claim 1 wherein the metal film includes regions repelling attachment of oligomers in multiple parallel rows aligned with the temperature gradient.

16. The apparatus of claim 1 further including an optical window positioned opposite the metal film with respect to the optical coupler for the detection of fluorescent tags on oligomers attached to the first face of the metal film.

17. A method of measuring sensor binding as a function of temperature using an apparatus having: a light source; a camera; an optical coupler positioned between the light source and the camera to receive light from the light source for reflection from an active face of the optical coupler to be received by the camera; a metal film extending along a measurement plane proximate to the active face for holding oligomers subject to interaction on a first face of the metal film; a flow channel opening against the first face of the metal film for receiving a liquid flow in a direction therealong; and a first and second thermal stabilizer positioned in thermal communication with the metal film and separated along the measurement plane near opposite edges of the metal film and adapted to establish a predetermined and substantially constant temperature gradient along the metal film; the method comprising the steps of:
   (a) applying a first biological oligomer to the first face of the metal film;
   (b) operating the first and second thermal stabilizers to provide a temperature gradient along the metal film;
   (c) flowing a liquid along the flow channel holding a material binding with the biological oligomer;
   (d) using the camera to measure reflected light at multiple points from the active face of the optical coupler while flowing the liquid; and
   (e) comparing the measured reflected light to gradient calibration data indicating a temperature associated with each of the multiple points to provide an indication of binding as a function of temperature.

18. The method of claim 17 further including the step of generating the gradient calibration data by:
   (i) operating the first and second thermal stabilizers to provide a uniform temperature along the metal film at successive different temperatures;
   (ii) measuring the reflected light from the active face of the optical coupler at each successive different temperatures to establish a temperature relationship between reflected light and temperature;
   (iii) operating the first and second thermal stabilizers to provide the substantially constant temperature gradient along the metal film; and
   (iv) measuring the reflected light from the active face of the optical coupler at the constant temperature gradient to deduce temperatures of the gradient from the temperature relationship between reflected light and temperature.

* * * * *